(12) United States Patent
Benner et al.

(10) Patent No.: US 8,614,072 B2
(45) Date of Patent: Dec. 24, 2013

(54) POLYMERASE INCORPORATION OF NON-STANDARD NUCLEOTIDES

(76) Inventors: Steven Albert Benner, Gainesville, FL (US); Zunyi Yang, Gainesville, FL (US)

( * ) Notice: Subject to any disclaimer, the term of this patent is extended or adjusted under 35 U.S.C. 154(b) by 54 days.

(21) Appl. No.: 12/999,138

(22) PCT Filed: Jun. 16, 2009

(86) PCT No.: PCT/US2009/003595
§ 371 (c)(1),
(2), (4) Date: Dec. 15, 2010

(87) PCT Pub. No.: WO2009/154733
PCT Pub. Date: Dec. 23, 2009

(65) Prior Publication Data
US 2011/0124053 A1    May 26, 2011

Related U.S. Application Data

(60) Provisional application No. 61/132,225, filed on Jun. 17, 2008.

(51) Int. Cl.
*C12P 19/34* (2006.01)
*C12Q 1/68* (2006.01)

(52) U.S. Cl.
USPC .......................... 435/91.1; 435/6.1; 435/91.2

(58) Field of Classification Search
USPC ........................................ 435/6.1, 91.1, 91.2
See application file for complete search history.

(56) References Cited

U.S. PATENT DOCUMENTS

| 8,053,212 B1 | 11/2011 | Benner |
| 2007/0087361 A1 | 4/2007 | Grenier et al. |

OTHER PUBLICATIONS

Yang, Z. et al. "Enzymatic incorporation of a third nucleobase pair" *Nucleic Acids Research*, 2007, pp. 4238-4249, vol. 35, No. 13.
Written Opinion in International Application No. PCT/US09/03595, Dec. 14, 2009, pp. 1-4.

*Primary Examiner* — Jezia Riley

(57) ABSTRACT

The disclosed invention teaches processes to amplify oligonucleotides by contacting templates and primers with DNA polymerases and triphosphates of non-standard nucleotides, which form nucleobase pairs fitting the standard Watson-Crick geometry, but joined by hydrogen bonding patterns different from those that join standard A:T and G:C pairs. Thus, this invention relates to nucleotide analogs and their derivatives that, when incorporated into DNA and RNA, expand the number of replicatable nucleotides beyond the four found in standard DNA and RNA. The invention further relates to polymerases that incorporate those non-standard nucleotide analogs into oligonucleotide products using the corresponding triphosphate derivatives, and more specifically, polymerases and non-standard nucleoside triphosphates that support the polymerase chain reaction (PCR), including PCR where the products contain more than one non-standard nucleotide unit.

20 Claims, 8 Drawing Sheets

A-Standard  A-AEGIS  B-Standard  B-AEGIS  C-Standard  C-AEGIS

In each set, amplification factor is 50.4 54.2 58.9 63.9

US 8,614,072 B2

POLYMERASE INCORPORATION OF NON-STANDARD NUCLEOTIDES

CROSS-REFERENCE TO RELATED APPLICATION

This application is the U.S. national stage application of International Patent Application No. PCT/US2009/003595, filed Jun. 16, 2009, which claims the benefit of U.S. Provisional Patent Application No. 61/132,225, filed Jun. 17. 2008, the disclosures of which are hereby incorporated by reference in their entirety, including all figures, tables and amino acid or nucleic acid sequences.

STATEMENT REGARDING FEDERALLY SPONSORED RESEARCH OR DEVELOPMENT

The United States Federal Government may have rights under this application.

THE NAMES OF THE PARTIES TO A JOINT RESEARCH AGREEMENT

Not applicable.

INCORPORATION-BY-REFERENCE OF MATERIAL SUBMITTED ON A COMPACT DISC

None

The Sequence Listing for this application is labeled "Seq-List.txt" which was created on Nov. 23,2010 and is 15 KB. The entire contents of the sequence listing is incorporated herein by reference in its entirety.

BACKGROUND OF THE INVENTION

1. Field of the Invention

This invention relates to processes that copy oligonucleotides in a polymerase chain reaction (PCR) where these oligonucleotides incorporate nucleotide analogs ("non-standard nucleotides") that form base pairs joined by hydrogen bonding patterns not found in standard nucleotides A, T, G and C. The invention relates more specifically to processes that amplify oligonucleotides holding more than one non-standard nucleotides, including non-standard nucleotides at adjacent positions in the oligonucleotides chain, and amplification in a nested PCR format.

2. Description of Related Art

Natural oligonucleotides bind to complementary oligonucleotides according to well-known rules of nucleobase pairing first elaborated by Watson and Crick, where adenine (A) pairs with thymine (T) (or uracil, U, in RNA), and guanine (G) pairs with cytosine (C), with anti-parallel complementary strands. In this disclosure, "DNA", "oligonucleotide", or "nucleic acid" is understood to include DNA and RNA, as well as derivatives where the sugar is modified, as in 2'-O-methyl and 2',3'-dideoxynucleoside derivatives, where the nucleobase has an appendage, and these nucleic acids and their analogs in non-linear topologies, including as dendrimers, comb-structures, and nanostructures, and analogs carrying appendages or tags (e.g., fluorescent, functionalized, or binding, such as biotin). Further, "polymerase" in this application is meant to include DNA polymerases of all families, RNA polymerases, and reverse transcriptases.

These pairing rules allow specific hybridization of oligonucleotides to complementary oligonucleotides, making oligonucleotides valuable as probes in the laboratory, in diagnostics, as messages that direct the synthesis of proteins, and in other applications known in the art. Such pairing is used, for example and without limitation, to capture oligonucleotides to beads, arrays, and other solid supports, allow nucleic acids to fold in hairpins, beacons, and catalysts, support function, such as fluorescence, quenching, binding/capture, and catalysis, and as part of complex structures, including dendrimers and nanostructures, and scaffolds to guide chemical reactions.

Further, base pairing underlies the enzymatic synthesis of oligonucleotides complementary to a template. Here, assembly of building blocks from nucleoside triphosphates is directed by a template to form a complementary oligonucleotide with a complementary sequence. This is the basis for replication in living systems, and underlies technologies for enzymatic synthesis and amplification of specific nucleic acids by enzymes such as DNA and RNA polymerase, the polymerase chain reaction (PCR), and assays involving synthesis, ligation, cleavage, immobilization and release, inter alia.

Watson-Crick pairing rules can be understood as the product of two rules of complementarity: (1) size complementarity (a big purine pairs with a small pyrimidine) and (2) hydrogen bonding complementarity (hydrogen bond donors pair with hydrogen bond acceptors). However, as noted by U.S. Pat. Nos. 5,432,272, 5,965,364, 6,001,983, 6,037,120, 6,140, 496, 6,627,456, and 6,617,106, Watson-Crick geometry can accommodate as many as 12 nucleobases forming 6 mutually exclusive pairs. Of these, four nucleobases forming two pairs are designated "standard", while eight nucleobases forming four pairs were termed "non-standard", and may be part of an "artificially expanded genetic information system" (AEGIS).

To systematize the nomenclature for the hydrogen bonding patterns, the hydrogen bonding pattern implemented on a small component of a nucleobase pair are designated by the prefix "py". Following this prefix is the order, from the major to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Following the prefix, hydrogen bond donor and acceptor groups are designated, from major to minor groove, by "A" and "D". Thus, the standard nucleobases adenine and guanine implement the standard hydrogen bonding patterns puDA- and puADD respectively.

A central teaching of this disclosure is that hydrogen-bonding patterns are distinct from the organic molecule that implemented them. Thus, guanosine implements the puADD hydrogen-bonding pattern. So does, however, 7-deazaguanosine, 3,7-dideazaguanosine, and many other purines and purine analogs, including those that carry side chains carrying functional groups, such as biotin, fluorescent, and quencher groups. Which organic molecule is chosen to implement a specific hydrogen-bonding pattern determines, in part, the utility of the non-standard hydrogen-bonding pattern, in various applications to which it might be applied.

Claims of U.S. Pat. No. 5,432,272 and its successors covered non-standard bases that implemented the pyDDA hydrogen bonding pattern. Subsequent efforts to use these, however, encountered problems, including epimerization [Voe96a,b], oxidation [Von95], and uncharacterized decomposition. Accordingly, Benner invented a new non-standard nucleoside, 6-amino-5-nitro-3-(1'-beta-D-2'-deoxyribofuranosyl)-2-(1H)-pyridone (dZ) to implement the pyDDA hydrogen bonding pattern. The nitro group rendered the otherwise electron-rich heterocycle stable against both oxidation and epimerization under standard conditions. When paired with a corresponding puAAD nucleotide, duplexes were formed with stabilities that, in many cases, were higher than those observed in comparable strands incorporating the dG:dC nucleobase pair [Yan06]. This invention is covered by U.S. patent application Ser. No. 11/372,400, which is incorporated herein by reference. Contents of this patent application have been published [Hut03].

While Z supports binding of oligonucleotides containing it to complementary strands that match a nucleobase implementing the puAAD hydrogen bond pattern, it was not clear that polymerases would accept this unnatural base pair. Polymerases are known to be idiosyncratic [Hor95], meaning that experimentation is necessary to ascertain whether a specific implementation of a non-standard hydrogen bonding scheme can be accepted by a polymerase.

Thus, it was necessary to show by experiment that polymerases could incorporate dZ and dP. This was done for oligonucleotides containing a single dZ or dP [Yan07], which was published less than a year before the priority date of the instant application. However, [Yan07] showed that the dZ and dP are lost in multiple PCR cycles with Taq and Deep Vent (exo−) polymerases, perhaps via a mechanism where deprotonated dZ mispairs with dG (or deprotonated dG pairs with dZ), while protonated dC mispairs with dP (or protonated dP pairs with dC). Thus, this art teaches away from any use of the non-standard dZ:dP nucleobase pair in higher level PCR, defined as PCR that creates amplicons with multiple non-standard nucleotides.

BRIEF SUMMARY OF THE INVENTION

This invention concerns processes that amplify oligonucleotides containing non-standard nucleotides (FIG. 1) in PCR where those oligonucleotides are not restricted in sequence to containing only a single nonstandard nucleotide, and where those oligonucleotides are not restricted in sequence to those where no adjacent nonstandard nucleotides appear, and amplification is done in a nested PCR format [Bro97].

DETAILED DESCRIPTION OF THE INVENTION

Figure 1:
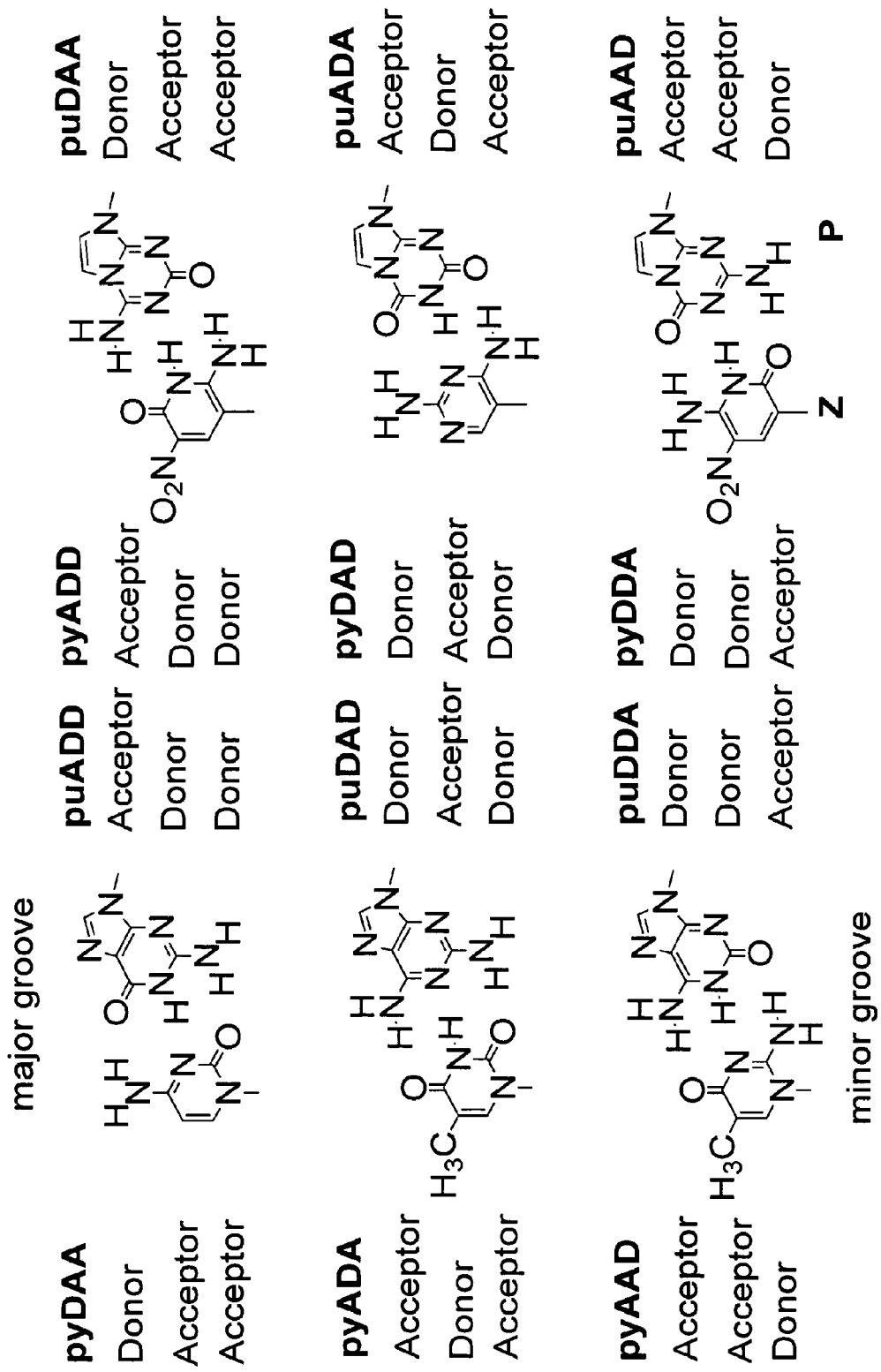
FIG. 1. A set of heterocycles implementing a set of hydrogen bonding patterns. The heterocycles used in the processes of the instant invention are labeled dZ and dP.

6-Amino-5-nitro-3-(1'-beta-D-2'-deoxyribofuranosyl)-2 (1H)-pyridone (dZ), its protected phosphoramidite derivatives suitable for chemical oligonucleotides synthesis, its triphosphate and its thiotriphosphate are reported in U.S. patent application Ser. No. 11/372,400 and in [Hut03]; both are incorporated herein by reference. Its complement, 2-amino-8-(1'-β-D-2'-deoxyribofuranosyl)-imidazo[1,2-α]-1,3,5-triazin-4(8H)-one (implementing puAAD, as dP) and these derivative are reported in [Hut03][Yan06], the synthetic procedures therein being incorporated herein by reference. These are preferred as non-standard nucleotides in the instant invention, although any non-standard nucleotide shown in FIG. 1 might be used in an eternal primer in a PCR.

It is known in art published less than a year before the priority date of the instant application [Yan07] that PCR amplification is possible for oligonucleotides that contain a single dP or a single dZ in the amplicon. However, the prior art shows that upon multiple PCR cycles, dP and dZ are removed from the amplicon. The instant invention was made following first the recognition it was possible to place dP and/or dZ in the PCR primers themselves. To amplify standard oligonucleotides, the dP and dZ would not be in the region of the primer that contacts that target, but rather within an oligonucleotide tag (or tail) appended to the 5'-end of the PCR primer that does contact the standard oligonucleotide target. PCR primers having two parts, a 5'-end containing dP and/or dZ (as well as standard nucleotides, optionally) and a 3'-end that is complementary to the target, are called "chimeric primers". PCR amplification with chimeric primers is then done in a nested fashion [Bro97]. Any loss of the non-standard nucleotide is restored in a subsequence PCR cycle, solving the loss problem described in the literature. After the chimeric primers are consumed in the first cycles, "external primers" having the sequence of only the 5'-tags continue the PCR.

Not known in any art published before the priority date of the instant application, and not anticipatable from the prior art given the idiosyncrasies of polymerases when challenged with unnatural nucleoside triphosphate substrates [Hor95], it was then discovered that PCR could succeed with certain polymerases even for amplicons that contain multiple dPs and/or multiple dZs. Further, we disclose here for the first time that certain polymerases support incorporation of adjacent dZs and adjacent dPs in prime extension reactions A third discovery was also unanticipated by us or the art. It turned out that by doing nested PCR with dZ and/or dP in the external primers, it was possible to obtain cleaner PCR products. Given this result, it became evident that PCR with dZ and dP in the primers was a useful, patentable invention, as is herein claimed.

Accordingly, the invention together with its associated discoveries provides a process for amplifying an oligonucleotide sequence in a PCR format, where a forward chimeric primer and a reverse chimeric primer are contacted with that target sequence. The forward chimeric primer is complementary to a region at the 3'-end of said sequence (as in any PCR), the reverse chimeric primer is identical in sequence to a region at the 5'-end of said sequence (as in any PCR), and the forward and reverse primers are joined at their 5'-prime ends to oligonucleotide tags having independently selected sequences that contain at least one non-standard nucleotide (see FIG. 1), where the presently preferred non-standard nucleotide is dZ or dP, most preferably dP. Then, as with standard OCR, the mixture is incubated the mixture with a DNA polymerase, RNA polymerase, or a reverse transcriptase, depending on the nature of the oligonucleotide to be amplified, together with the triphosphates needed to complement the nucleotides in the primers and sequence. The presently preferred polymerases are Phusion and Vent or Deep Vent having exonuclease activity, as described further in the examples. This process, of course, comprises a simpler PCR process that amplifies an oligonucleotide sequence that contains one or more non-standard nucleotides, preferably dZ or dP. PCR amplification of an oligonucleotide containing just one was disclosed less than a year before the priority date in [Yan07], and therefore is patentable under United States law. PCR amplification of oligonucleotides containing more than one non-standard nucleotide and adjacent non-standard nucleotides was not in the prior art prior to the priority date, and is not rendered obvious by [Tan07], and is therefore internationally patentable.

EXAMPLES

Example 1

PCR with dZ and dP

This example demonstrates that chimeric primers containing dZ and dP in their external segments support PCR. The following oligonucleotides were prepared by phosphoramidite synthesis. These include two reverse chimeric primers, identical except that in R-36-Nest, some of the G's were replaced by P's in the segment not complementary to the template:

```
R-36-Std:
                                          SEQ ID 1
3'-CCATGGTAGCTATGCGCAACGCTAGCGAGGAAGGAC-5'-P32

R-36-Nest:
                                          SEQ ID 2
3'-CCATGGTAGCTATGCGCAACPCTAPCGAPGAAPGAC-5'-P32
``` a pair of complementary template sequences:

```
Temp-R-47:
                                          SEQ ID 3
5'-CCATGGGAGACCGCGGTGGGCCCGGCCGGGTACCATCGATACGCG
TT-3'

Temp-F-47:
                                          SEQ ID 4
3'-GGTACCCTCTGGCGCCACCCGGGCCGGCCCATGGTAGCTATGCGC
AA-5'
``` and two forward chimeric primers, one with the same replacements:

```
(F-34-Nest)
5'-CTAPGACPACGPACTPCCCATGGGAGACCGCGGT-3'  SEQ ID 5

(F-34-Std)
5'-CTAGGACGACGGACTGCCCATGGGAGACCGCGGT-3'  SEQ ID 6
```

The underlined portions of the primers are complementary to the template. The portions not underlined are the tags that contain non-standard nucleotides. In separate experiments the chimeric and non chimeric primers were incubated under the following conditions:

| Components | Volume (μl) | Final Concentration |
|---|---|---|
| Nuclease-Free Water (final volume of 20 μl) | 1.6 | |
| Forward Primer: F-34-Nest (2 pmol/μl) | 5 | 500 nM |
| Reverse Primer: R-36-Nest (1 pmol/μl, radiolabeled) | 1 | 50 nM |
| Reverse Primer: R-36-Nest (1.5 pmol/μl) | 6 | 450 nM |
| Template: Temp-F-47(1 pmol/μl) Temp-R-47(1 pmol/μl) | 0.1 for each | 5 nM |
| 10 × Reaction Buffer | 2 | 1× |
| dNTP (2 mM of each dNTP) | 2 | 0.1 mM each |
| dZTP (2 mM) or Water (for negative control) | 2 | 0.1 mM |
| Taq (5 U/μl) | 0.2 | 0.05 U/μl |

Figure 3:
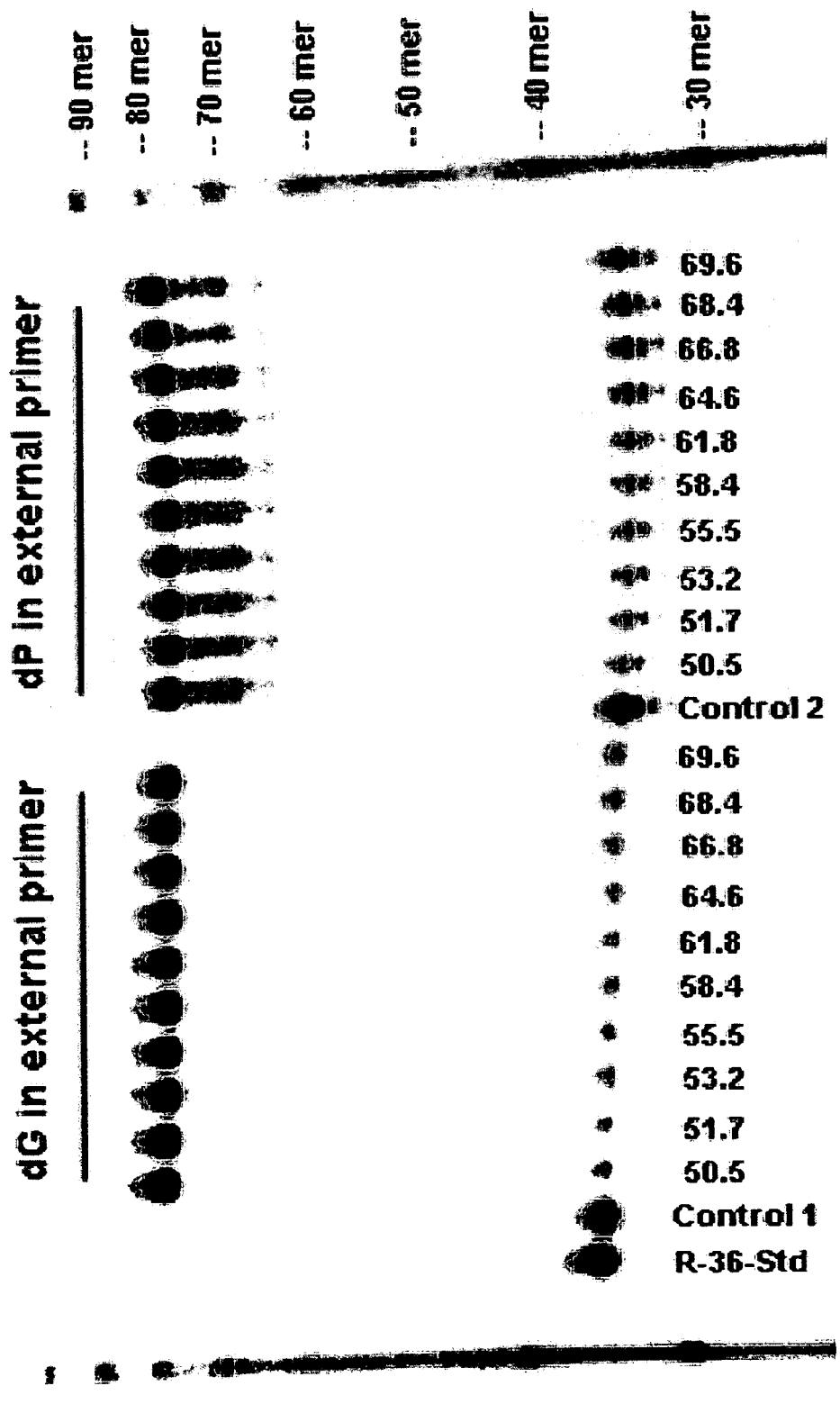
FIG. 3. Autoradiograph of an electrophoresis gel showing PCR products as described in Example 1. _Left: PCR using primers only standard nucleotides in both the amplicon binding region and in the 5'-tag. Right. PCR using primers containing dP in the 5'-tag.

The products were resolved by gel electrophoresis (FIG. 3). These results show that primers containing multiple dP's support PCR works. The experiment does not show, however, that primers containing consecutive dPs effectively support PCR.

Example 2

Nested PCR

Figure 2:
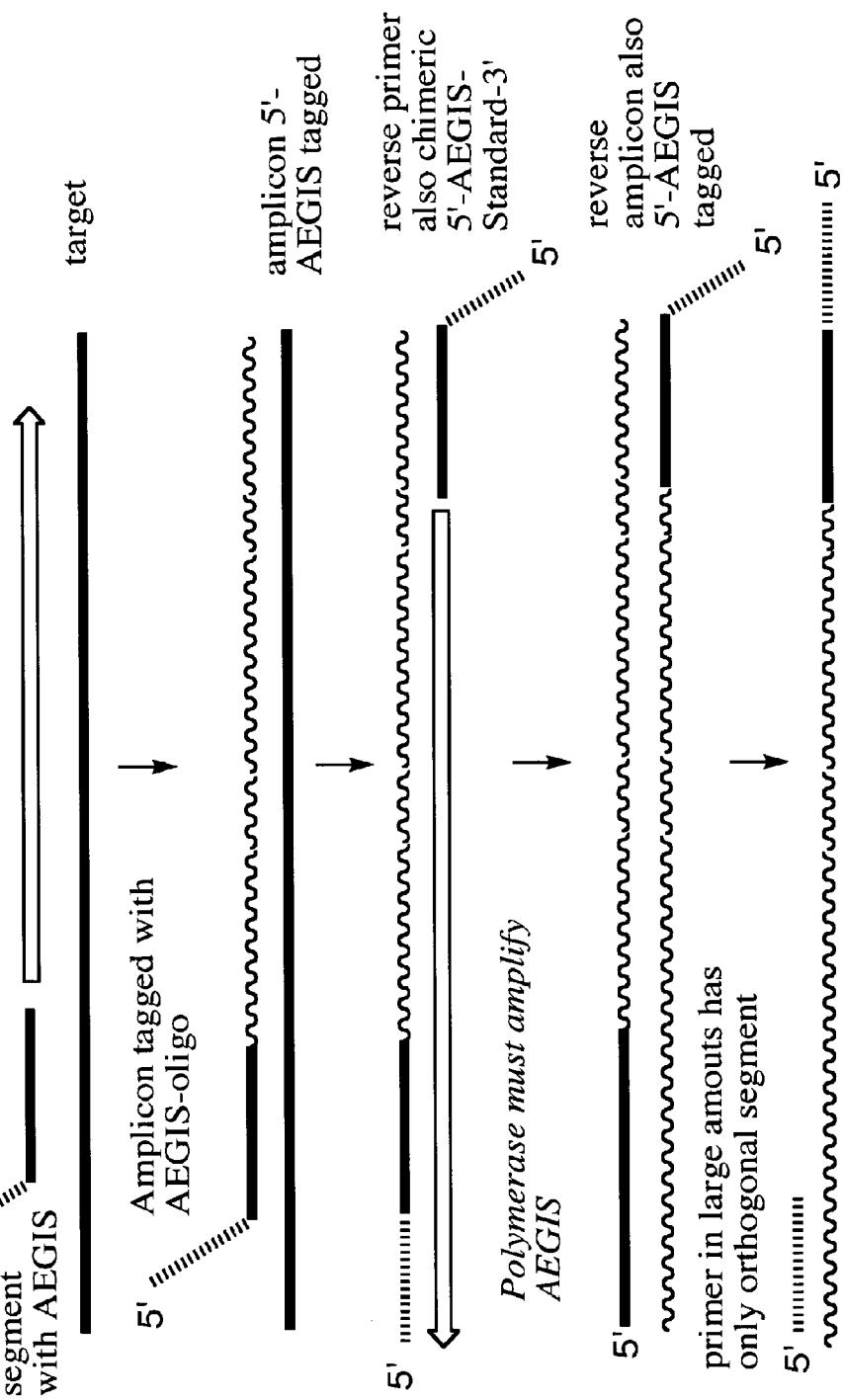
FIG. 2. Schematic showing nested PCR, where nucleotides from an artificially expanded genetic information system (AEGIS) are included in the tags (vertically hashed lines) attached to chimeric PCR primers. Chimeric primers initiating the PCR may be at low concentrations, diminishing the possibility of off-target priming. After their consumption in early PCR cycles, PCR continues via priming with external primers.

This experiment demonstrated the use of dZ and dP pairing in the external segments of a nested PCR [Bro97], shown schematically in FIG. 2. The following oligonucleotides were prepared by phosphoramidite synthesis. These were set up in three set of nested PCR experiments. The first used external primers, one containing dP, the other not:

```
F-17-Nest
32P-5'-CTAPGACPACGPACTPC-3'           SEQ ID 7

F-17-Std
32P-5'-CTAGGACGACGGACTGC-3'           SEQ ID 8
``` applied in a direct PCR experiment for a longer template that included Temp-R-47 in its middle:

```
Temp-R-81:
                                          SEQ ID 9
5'-CTAGGACGACGGACTGCCCATGGGAGACCGCGGTGGGCCCGGCCG

GGTACCATCGATACGCGTTGCGATCGCTCCTTCCTG-3'
``` and two reverse external primers, one containing dP, the other not:

```
R-17-Std:
3'-CGCTAGCGAGGAAGGAC-5'               SEQ ID 9

R-17-Nest:
3'-CPCTAPCGAPGAAPGAC-5'               SEQ ID 10
```

These were incubated using the following procedure in Experiment A.

| Components | Volume (μl) | Final Concentration |
|---|---|---|
| Nuclease-Free Water (final volume of 20 μl) | 7.65 | |
| Forward Primer: F-17-Std or Nest (2 pmol/μl) | 2.25 | 225 nM |
| Forward Primer: F-17-Std or Nest (1 pmol/μl, radiolabeled) | 0.5 | 25 nM |
| Reverse Primer: R-17-Std or Nest (2 pmol/μl) | 2.5 | 250 nM |
| Template: Temp-R-81 (0.01 pmol/μl) | 0.5 | 0.25 nM |
| 10 × Reaction Buffer (MgCl$_2$ (15 mM)) | 2 | 1 × (MgCl$_2$ (1.5 mM)) |
| MgCl$_2$ (25 mM) | 0.4 | MgCl$_2$ (0.5 mM) |
| dNTP (2 mM of each dNTP) | 2 | 0.2 mM each |
| dZTP (2 mM) | 2 | 0.2 mM |
| Taq (5 U/μl) | 0.2 | 0.05 U/μl |

Figure 4:
FIG. 4. Autoradiograph of an electrophoresis gel showing nested PCR products obtained as described in Example 2.

The standard primers F-17-Std and R-17-Std should amplify the Temp-R-81 target, leading to a band in a gel electrophoresis resolution that migrates as an 81-mer. This is in fact the case (FIG. 4, A-Std lane). If dP does not bind to dC, then the AEGIS dP-containing primers should not yield and 81-mer band. This is also the case (FIG. 4, A-AEGIS).

In another experiment, the following recipe was used in a nested PCR experiment:

| Components | Volume (μl) | Final Concentration |
|---|---|---|
| Nuclease-Free Water (final volume of 20 μl) | 6.65 | |
| Forward Primer: F-17-Std or Nest (2 pmol/μl) | 2.25 | 225 nM |
| Forward Primer: F-17-Std or Nest (1 pmol/μl, radio-labeled) | 0.5 | 25 nM |
| Reverse Primer: R-17-Std or Nest (2 pmol/μl) | 2.5 | 250 nM |
| Template: Temp-R-47 (0.01 pmol/μl) | 0.5 | 0.25 nM |
| F-34-Std or F-34-Nest (0.1 pmol/μl) | 0.5 | 2.5 nM |
| R-36-Std or R-36-Nest (0.1 pmol/μl) | 0.5 | 2.5 nM |
| 10 × Reaction Buffer (MgCl$_2$ (15 mM)) | 2 | 1 × (MgCl$_2$ (1.5 mM)) |
| MgCl$_2$ (25 mM) | 0.4 | MgCl$_2$ (0.5 mM) |
| dNTP (2 mM of each dNTP) | 2 | 0.2 mM each |
| dZTP (2 mM) | 2 | 0.2 mM |
| Taq (5 U/μl) | 0.2 | 0.05 U/μl |

Note:
1 × standard Taq Reaction Buffer (10 mM Tris-HCl, 50 mM KCl, 1.5 mM MgCl$_2$, pH 8.3 at 25° C.).
1 × ThermoPol Reaction Buffer (20 mM Tris-HCl, 10 mM (NH$_4$)$_2$SO$_4$, 10 mM KCl, 2 mM MgSO$_4$, 0.1% Tritonx-100, pH 8.8 at 25° C.).

Experiment B used F-34-Std and R-36-Std as chimeric primers. These should generate products when amplified with external primers built without dP, but not when amplification was sought with external primers containing dP. This was in fact the case (FIG. 4, B-Std and B-AEGIS, respectively). Experiment C used F-34-Nest and R-36-Nest as chimeric primers. These should not generate products when amplified with external primers built with dP, but should generate when amplification was sought with external primers containing dP. This was in fact the case (FIG. 4, C-Std and C-AEGIS, respectively). These experiments shows showed the ability of DNA polymerase to support a six letter PCR with dA, dT, dG, dC, dZ, and dP as the six letters. They also demonstrate the orthogonality of the process. Nested PCR works with AEGIS external primers when it should and not when it should not, and vice versa.

Example 3

Primer Extension Through Adjacent dZs in a Template

Given the well-known idiosyncrasies of polymerases and the possibility of strong neighbor effects [Hor95], it was not clear that these results would be extendable to PCR amplifications where dZ or dP are adjacent in a template, requiring the incorporation of dP and dZ adjacent in the template. The following experiments were done to screen thermophilic polymerases for their ability to incorporate dPTP opposite dZ in the template. This was done at the following concentrations: [dATP]=[dCTP]=[dTTP]=100 microM), dGTP (5 microM to 100 microM), or dPTP (5 microM to 100 microM) at pH7.0 or 7.5, with the following oligonucleotides (R-19-S was P-32 labeled at its 5'-end):

R-19-S:
SEQ ID 11
5'-GGTACCATCGATACGCGTT-3'

R-36-Nest-6Z:
SEQ ID 12
3'-CCATGGTAGCTATGCGCAAGTZZTTZZTCGZTAGZG-5'

5'-$^{32}$P-labeled primer R-19-S (2 pmole, final assay concentration 50 nM) was annealed to a template sequence R-36-Nest-6Z (3 pmole, final assay concentration 75 nM) by heating (5 min 95° C.) and then slow cooling (0.5 h) to room temperature. dATP, dTTP and dCTP (4 nmole each, final 100 microM) and dGTP (final 10 microM), or dPTP (final 10 microM) were added at room temperature. The reaction mixture was pre-incubated at 72° C. for 30 seconds and followed by the addition of Taq DNA polymerase to give a final volume of 40 microL. The mixture was incubated at 72° C. for 4 minutes, and quenched by dilution into PAGE loading/quench buffer (10 microL, 10 mM EDTA in formamide). Samples were resolved by electrophoresis using a 14% PAGE (7 M urea). The gel was analyzed using MolecularImager software.

Figure 5:
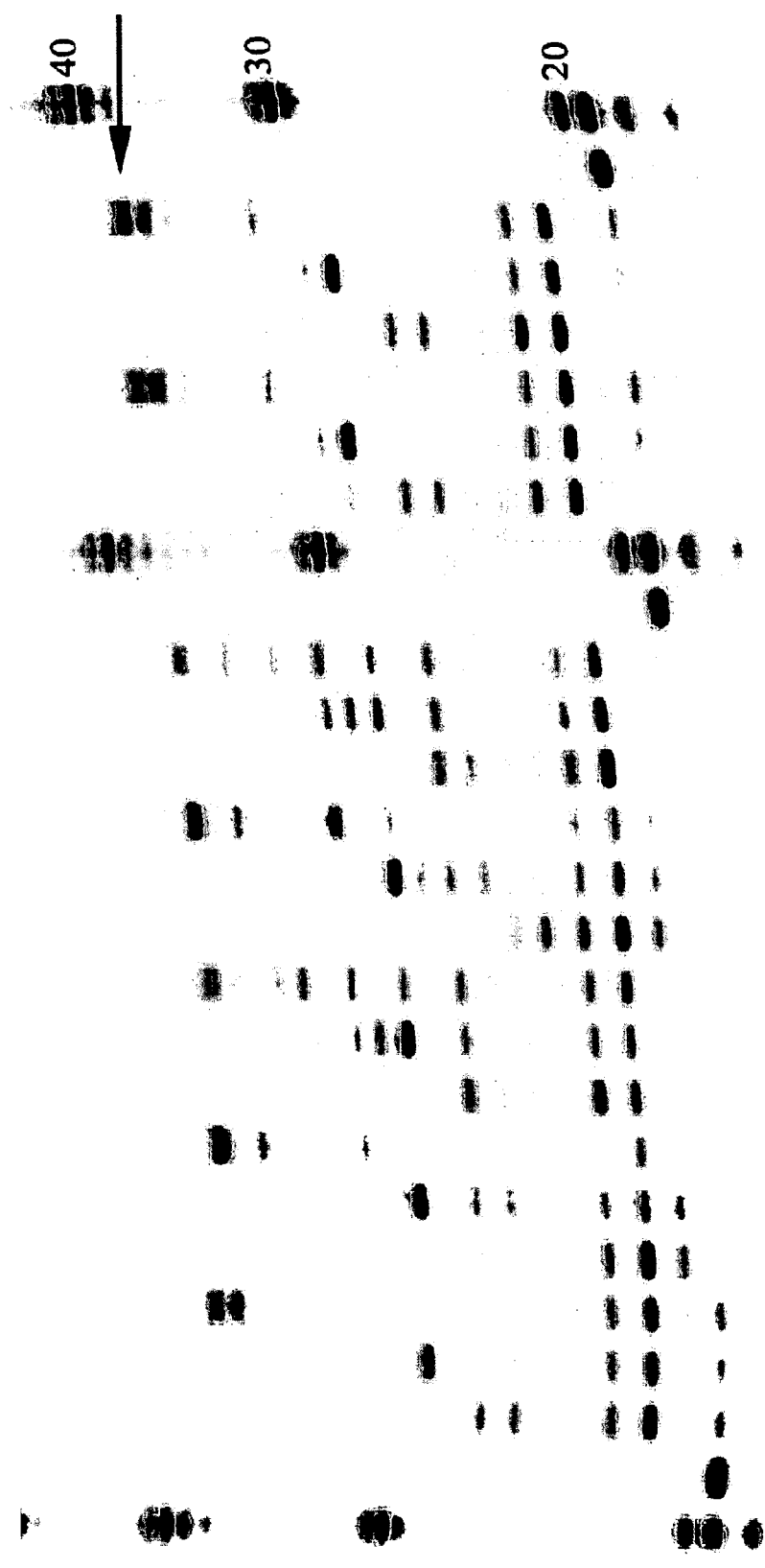
FIG. 5. Autoradiograph of an electrophoresis gel showing primer extension products obtained as described in Example 3 from amplicons containing adjacent dZs.
Figure 6:
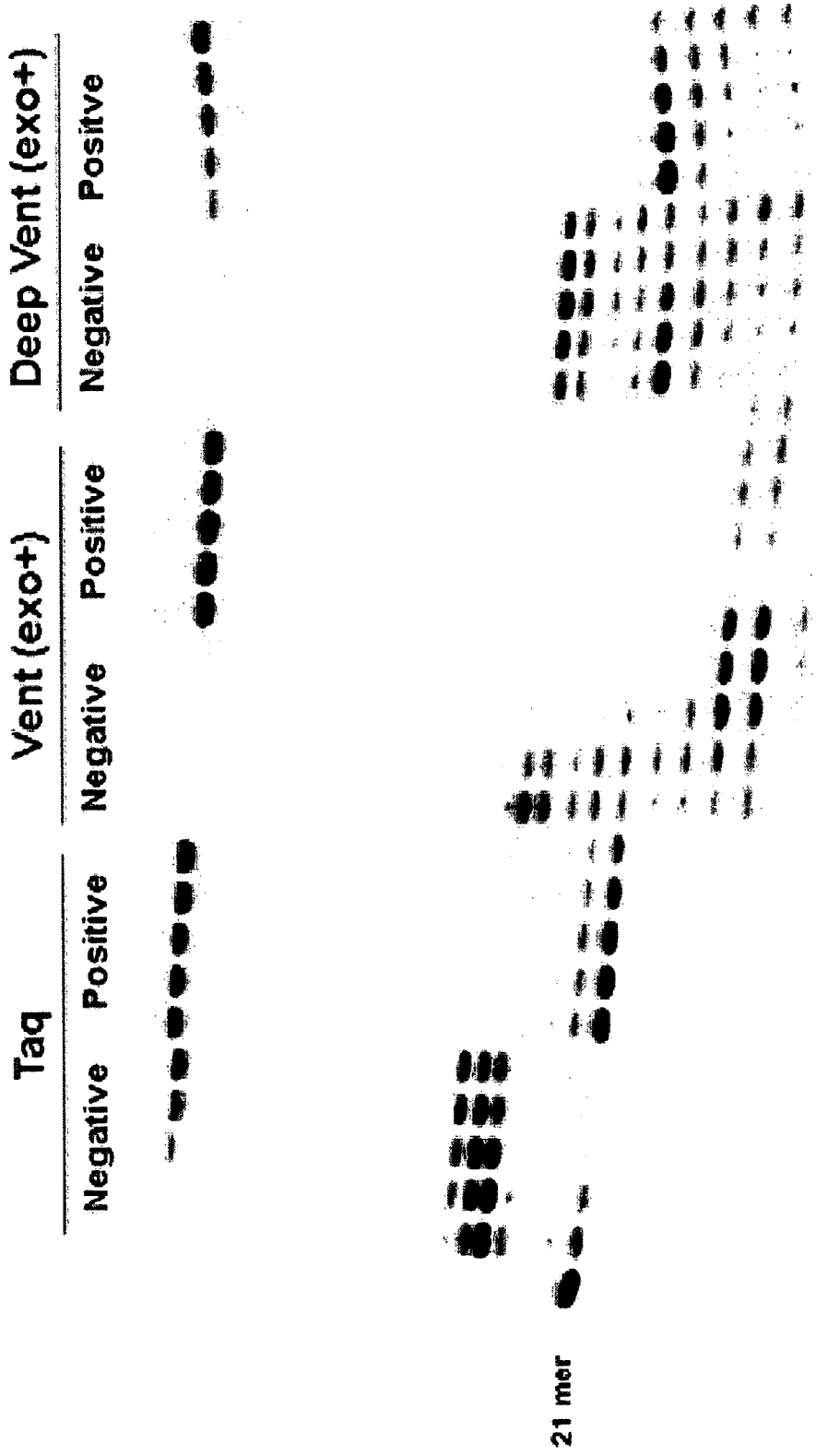
FIG. 6. Autoradiograph of an electrophoresis gel showing primer extension products obtained as described in Example 4.

These results (FIG. 5) showed that Vent and Deep Vent performed better than Taq. Without wishing to be bound by theory, this may be due to their exonuclease activities.

Example 4

Incorporation of dZTP Opposite Consecutive Template dPs

To compare the efficiency and fidelity of DNA polymerases (Taq, Vent (exo+), and DV (exo+)) incorporating dZTP opposite two consecutive dPs in a template, 5'-$^{32}$P-labeled primer T7-Y-RS-S16 (0.2 pmole of hot primer plus 4 pmole of cold primer, final assay concentration 70 nM) was annealed to template T7-PP-Temp (6 pmole, final assay concentration 100 nM) in 1×. Thermopol polymerase reaction buffer (20 mM Tris-HCl, 10 mM (NH$_4$)$_2$SO$_4$, 10 mM KCl, 2 mM MgSO$_4$, 0.1% Triton X-100, pH=8.0 at room temperature) by heating (5 min at 95° C.) and then slow cooling (0.5 h) to room temperature. dNTP (each final 0.1 mM) and dZTP (final 0.1 mM, with (+) or without (−)) were added at room temperature. The reaction mixture was cooled to 4° C. for 1 min and followed by the addition of Taq (2.5 units), Vent (exo+), or Deep Vent (exo+) DNA polymerase (2 units for Vent and Deep Vent) to give a final volume of 60 microL. The primer was extended at 65° C. and aliquots (7 microL) were taken from each reaction at time intervals (1, 2, 4, 8, and 16 min), quenched by PAGE loading/quench buffer (7 microL, 10 mM EDTA in formamide) and resolved by electrophoresis using a 16% PAGE (7 M urea). The gel was analyzed using MolecularImager. These oligonucleotides were used:

```
Negative control (-): dNTP (each 0.1 mM)
T7-Y-RS-S16:
                                         SEQ ID 13
3'-GAAAT*CACTCCCAATTAAGCG-5'

T7-PP-Temp:
                                         SEQ ID 14
5'-GCGTAATACGACTCACTATAGACGAPPCTACTTTAGTGAGGGTTA
ATTCGC-3'

Positive control (+): dNTP (each 0.1 mM), and
dZTP (0.1 mM)
T7-Y-RS-S16:
                                         SEQ ID 15
3'-GAAAT*CACTCCCAATTAAGCG-5'

T7-PP-Temp:
                                         SEQ ID 16
5'-GCGTAATACGACTCACTATAGACGAPPCTACTTTAGTGAGGGTTA
ATTCGC-3'
```

The order of performance of the polymerases tested is Deep Vent (exo+)>Vent (exo+)>Taq. In the absence of dZTP, Deep Vent and Vent misincorporates only one dCTP opposite the first dP. However, Taq can misincorporate dCTP opposite two consecutive dPs, and then keep extending primer. All are better than exo(−) polymerases (not reported in [Yan07]).

Example 5

PCR with Amplicons Containing Multiple Adjacent dPs and dZs

To compare the outcome of PCR with templates containing one or two adjacent dPs, the following oligonucleotides were prepared:

```
T7-Z-RS-S16:
                                         SEQ ID 17
5'-GCGTAATACGACTCAC*TATAG-3'
(Template-A)

T7-G-51-Std:
                                         SEQ ID 18
5'-GCGTAATACGACTCACTATAGACGAGCGTACTTTAGTGAGGGTTA
ATTCGC-3'
(Template-B)

T7-P-Temp:
                                         SEQ ID 19
5'-GCGTAATACGACTCACTATAGACGAPCGTACTTTAGTGAGGGTTA
ATTCGC-5'
(Template-C)

T7-PP-Temp:
                                         SEQ ID 20
5'-GCGTAATACGACTCACTATAGACGAPPCTACTTTAGTGAGGGTTA
ATTCGC-3'

T7-Y-RS-S16:
                                         SEQ ID 21
3'-GAAAT*CACTCCCAATTAAGCG-5'
```

These were incubated under the following conditions:

| Components | Volume (μl) | Final Concentration |
|---|---|---|
| Nuclease-Free Water (final volume of 40 μl) | 17 | |
| Forward Primer: T7-Z-RS-S16 (10 pmol/μl) | 1 | 0.25 μM |
| Reverse Primer: T7-Y-RS-S16 (10 pmol/μl) | 1 | 0.25 μM |
| Template: Three different Templates (A, B, and C) (0.01 pmol/μl) | 1 + 4 (H2O) | 0.25 nM |
| 10 × Thermopol Buffer (pH = 8.0) | 4 | |
| dNTP (2 mM) | 4 | 0.2 mM each |
| dZTP (2 mM) | 4 | 0.2 mM |
| dPTP (2 mM) | 4 | 0.2 mM |
| Hot Start Taq (5 U/μl) | 0.5 | 0.06 U/μl |

ThermoPol Reaction Buffer (20 mM Tris-HCl, 10 mM (NH$_4$)$_2$SO$_4$, 10 mM KCl, 2 mM MgSO$_4$, 0.1% Triton X-100, pH 8.0 at 25° C.).
PCR: one cycle of 95° C. for 15 min; 26 cycles of 95° C. for 20 s, (55° C. for 30 s, 72° C. for 1 min or 2 min; 72° C. for 5 min; then stored at 4° C.

Figure 7:
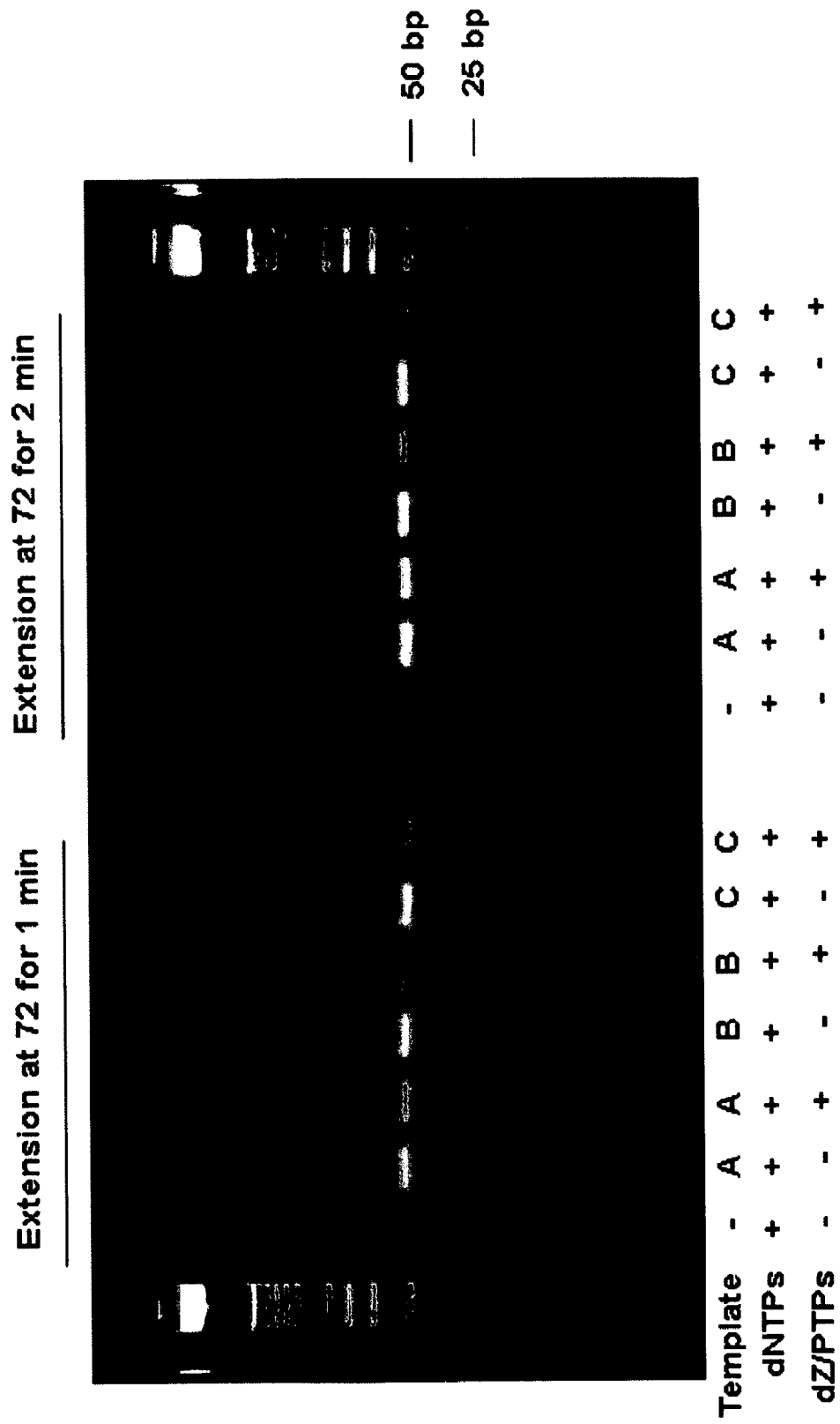
FIG. 7. Autoradiograph of an electrophoresis gel showing PCR products obtained as described in Example 5

The results are shown in FIG. 7. All PCRs generates some degree of 51-mer product. Template A contained only standard nucleotides. Template B contained a single dP. Template C contained a series of dPs, including two adjacent dPs.

Example 6

Prevention of Primer Dimerization with AEGIS Containing Primers

To demonstrate that if dP or dZ were incorporated into PCR primers in place of one or more dGs or dCs, then the synthetic primers containing dPs or dZs would not find their perfectly matched complementary strands in a primer pool, a 17-mer, 5'-CAGGAAGGAGCGATCGC-3' (SEQ ID 35) was deliberately designed to form a self-dimer with 8 base pairs at the 3'-end (underline region, $T_m$=32° C.), and subjected to PCR conditions. As expected, primer-dimer formed rapidly. In contrast, perfectly mismatched primers 5'-CAGGAAG-GAGCPATCPC-3' (SEQ ID 36) and 5'-CAGGAAGGAGZ-GATZGC-3' (SEQ ID 37), which would form primer-dimers only by mismatching dP with dC (in the first case) and dZ with dG (in the second) gave no detectable amplicon under the same conditions, even after 45 cycles.

Example 7

Preferred DNA Polymerases and Optimized Amplification Conditions

With several polymerases able to replicate efficiently DNA fragments containing multiple dPs and dZs, the preferred polymerase having the highest PCR efficiency to amplify target using a nested PCR architecture with AEGIS nucleotides in the external primers was determined. Taq, 9° N, Deep Vent (both exo$^+$ and exo$^-$), Vent (both exo$^+$ and exo$^-$), Phusion, and Herculase were tested; the PCR efficiency was monitored by real-time PCR. The polymerase has the higher PCR efficiency generates more PCR amplicon and producing higher fluorescence signal at an earlier cycle of the PCR. Phusion was found to have the highest PCR efficiency among the polymerases tested with proofreading activity; Deep Vent (exo$^-$) is the most efficient among all the polymerases without exonuclease activity. For all polymerases tested, dP-containing nested PCR, in general, has higher PCR efficiency than that of the dZ-containing nested PCR.

Phusion DNA polymerase generates long templates with an accuracy and speed previously unattainable with a single enzyme. In addition, the error rate of Phusion is 50-fold lower than that of Taq, and about 6-fold lower than that of Vent and Deep Vent. Therefore, Phusion DNA polymerase was further optimized as a presently preferred polymerase for nested PCR with dP-containing external primers. The major infidelity during the 6-nucleotide PCR arises from misincorporation of dGTP opposite template dZs or dZTP opposite template dGs. This infidelity is pH dependent, when the pH of the buffer is low, the rate of misincorporation decreases.

To determine a preferred pH for PCR efficiency and fidelity, three types of nested PCR were conducted with Phusion HF buffer at four different pH values (7.0, 7.5, 8.0, and 8.5). Amplification was monitored by the real-time PCR with SYBR Green. For "type A" nested PCR, standard external and chimeric primers and four standard nucleotide triphosphates (dNTPs) were used; amplification curves in real-time show that PCR efficiency increases when the pH of the buffer decreases. After 30 cycles, the melting temperature of each PCR amplicon was measured and the size of each amplicon was analyzed by agarose (3%) gel. The $T_m$ of each PCR amplicon generated under four different pH values is roughly the same (about 91.49±0.5° C.).

The type B nested PCR is identical to the type A nested PCR, except that dZTP was also included into the reaction. By comparing the melting temperature of each PCR amplicon in the type B reaction with that of the type A reaction, misincorporation of dZTP at different pHs was measured. The $T_m$ of the amplicon improves as the pH of the reaction buffer decreases. For example, at the highest pH value tested (8.5), the $T_m$ of the PCR amplicon is 3.75±0.05° C. below than that of the control PCR (type A); at the lowest pH value (7.0), the $\Delta T_m$ was to 0.29±0.05° C. below the fully standard PCR. For the type C nested PCR, dP-containing primers were used instead of standard primers, and PCR amplifications were conducted under the same conditions as type B nested PCR. The $T_m$ of each PCR amplicon increases as the pH value of the reaction buffer decreases; the effect of pH on PCR efficiency and misincorporation of dZTP opposite template dG agreed with that with type B nested PCR. However, the $T_m$ of each PCR amplicon in the type C nested PCR is higher (about 3.6° C.) than in type B nested PCR, this enhancement of the $T_m$ is mainly due to the higher thermostability of the Z:P base pairs in the PCR amplicon.

The PCR amplicons obtained at four different pHs in type B nested PCR were cloned, and their sequences were verified by Sanger sequencing. This shows that misincorporation of dZTP opposite template G is insignificant and does not prevent the PCR amplicon of interest to be cloned and sequenced using the conventional Sanger method. This too was not expected given [Yan07], and can be used as a restrictive element of a claim.

Example 8

Nested PCR with AEGIS External Primers Cleans Up Multiplexed PCR

To show whether the dP-containing nested PCR can enhance the capability of multiplexed PCR, this system was applied to human genomic DNA, targeting the three genes associated with cancer: TOP1, HBEGF, and MYC. The oligonucleotides used in this experiment were:

```
Top-F-External
                                           SEQ ID 22
5'-TPTAPATTTPTATPTATPTATPAT-3'

Top-F-Chimeric
                                           SEQ ID 23
5'-TPTAPATTTPTATPTATPTATPATGACAGCCCCGGATGAGAAC-3'

TOP-R-Chimeric
                                           SEQ ID 24
3'-GTTAGCTCGACAACGTTAAGAACAPAGGPAAATPACTCPCA-5'

Universal-R-4P
                                           SEQ ID 25
3'-CAPAGGPAAATPACTCPCA-5'

HBE-F-External
                                           SEQ ID 26
5'-AAAPTATAPTAAPATPTATAPTAG-3'

HBE-F-Chimeric
                                           SEQ ID 27
5'-AAAPTATAPTAAPATPTATAPTAGCCCCAGTTGCCGTCTAGGA-3'

HBE-R-Chimeric
                                           SEQ ID 28
3'-TTCACGGTTTGTCTCATACAGGCCAPAGGPAAATPACTCPCA-5'

Universal-R-4P
                                           SEQ ID 29
3'-CAPAGGPAAATPACTCPCA-5'

MYC-F-External
                                           SEQ ID 30
5'-GTATTTPAPTAAPTAATTPATTPA-3'

MYC-F-Chimeric
                                           SEQ ID 31
5'-GTATTTPAPTAAPTAATTPATTPATCCTCCTTATGCCTCTATC
AT-3'

MYC-R-Chimeric
                                           SEQ ID 32
3'-CCTGAGAACTAGTTTCGCGCCCAPAGGPAAATPACTCPCA-5'

Universal-R-4P
                                           SEQ ID 33
3'-CAPAGGPAAATPACTCPCA-5'
```

The external primers were adopted from Luminex's 5'-universal tag sequences, which were designed by the company to have unique sequences to avoid cross-hybridization and have roughly equal melting temperatures. To design the chimeric primers, universal external primer was added to either forward or reverse gene-specific primers, the other three external primers were also attached to gene-specific primers, the combination of each external primer to a certain gene-specific primer was optimized using primer design software (Oligo-Analyzer 3.1), and following the general principles of multiplex PCR primer design to avoid cross-hybridization and hairpin structure of primers.

Figure 8:
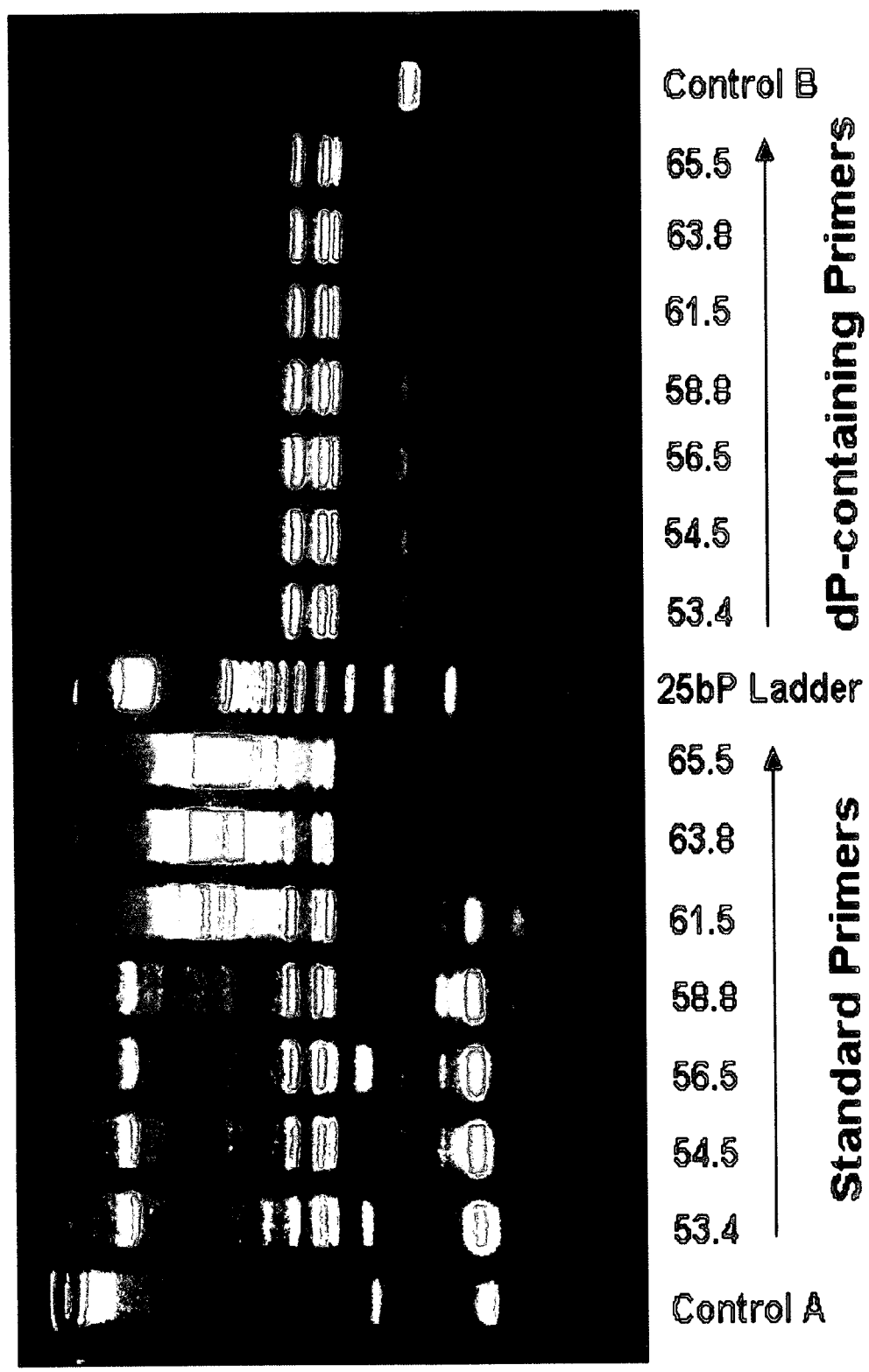
FIG. 8. Autoradiograph of an electrophoresis gel showing that nested PCR external primers containing AEGIS components produces cleaner PCR products (right) than with standard external primers (left).

Three cancer genes in human genomic DNA were multiplexed amplified by standard nested PCR and dP-containing nested PCR using Phusion under seven different annealing temperatures. As shown in FIG. 8, standard nested PCR with all annealing temperatures give messy PCR results (left): at the lower annealing temperatures (from 53.4° C. to 58.8° C.), significant amounts of primer dimer (about 40 nucleotides in length) were generated; at the higher annealing temperatures (from 61.5° C. to 65.5° C.), non-specific PCR artifacts (PCR amplicons longer than the desired length) were produced along with the disappearance of the primer dimer.

However, the dP-containing nested PCR generated the desired PCR amplicons with minimal PCR artifacts (right). For the two control reactions (without genomic DNA), control A (standard nested PCR) gave some primer dimers (a 40-mer amplicon formed by standard external primers) and significant amount of long PCR amplicons, which may caused by the further priming from the primer dimer. The control B (dP-containing nested PCR) gave one band, which was formed by the dimerization of the dP-containing chimeric primers, as the 3'-ends of the chimeric primers are the standard gene-specific oligonucleotides. This dimerization could be further eliminated by reducing the concentration of the dP-containing chimeric primers. We further verified that the dP-containing multiplexed nested PCR also performed better than the standard nested PCR under HF Phusion buffer with other different pH values (8.5, 8.0, and 7.5).

This result was entirely unanticipated. Nested PCR using AEGIS external primers leads to cleaner multiplexed PCR. Without wishing to be bound by theory, this may arise because even with standard primers not having exact matched in a genome, standard primers have sufficient mismatches to prime at off-target sites.

LITERATURE CITED

[Bro97] Brownie, J., Shawcross, S., Theaker, J., Whitcombe, D., Ferrie, R., Newton, C., Little, S. (1997). *Nucleic Acids Res.* 25, 3235-3241

[Hor95] Horlacher, J., Hottiger, M., Podust, V. N., Hübscher, U., Benner, S. A. (1995) *Proc. Natl. Acad. Sci.,* 92, 6329-6333

[Hut03] Hutter, D. and Benner, S. A. (2003) *J. Org. Chem.,* 68, 9839-9842

[Swi89] Switzer, C. Y., Moroney, S. E., Benner, S. A. (1989) Enzymatic incorporation of a new base pair into DNA and RNA. *J. Am. Chem. Soc.* 111, 8322-8323

[Voe96a] Voegel, J. J., Benner, S. A. (1996) *Helv. Chim. Acta* 79, 1863-1880

[Voe96b] Voegel, J. J., Benner, S. A. (1996) *Helv. Chim. Acta* 79, 1881-1898

[Voe93] Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547

[Von95] von Krosigk, U., Benner, S. A. (1995) *J. Am. Chem. Soc.* 117, 5361-5362

[Yan06] Yang, Z., Hutter, D., Sheng, P., Sismour, A. M. and Benner, S. A. (2006) *Nucleic Acids Res.,* 34, 6095-6101.

[Yan07] Yang, Z., Sismour, A. M., Sheng, P., Puskar, N. L., Benner, S. A. (2007) *Nucl. Acids Res.* 35, 4238-4249

What is claimed is:

1. A process for amplifying an oligonucleotide sequence, said process comprising contacting said oligonucleotide sequence in aqueous solution with a forward primer comprising a first part at its 5'-end and a second part at its 3'-end, a reverse primer comprising a first part at its 5'-end and a second part at its 3'-end, a forward external primer identical in sequence to a segment within the first part of the forward primer, and a reverse external primer identical in sequence to a segment within the first part of the reverse primer, wherein the second part of said forward primer is complementary to a region at the 3'-end of said oligonucleotide sequence, wherein the second part of the reverse primer is identical in sequence to a region at the 5'-end of said oligonucleotide sequence, wherein the forward external primer and reverse external primer have independently selected sequences that contain at least one non-standard nucleotide incorporating a nucleobase selected from the group consisting of

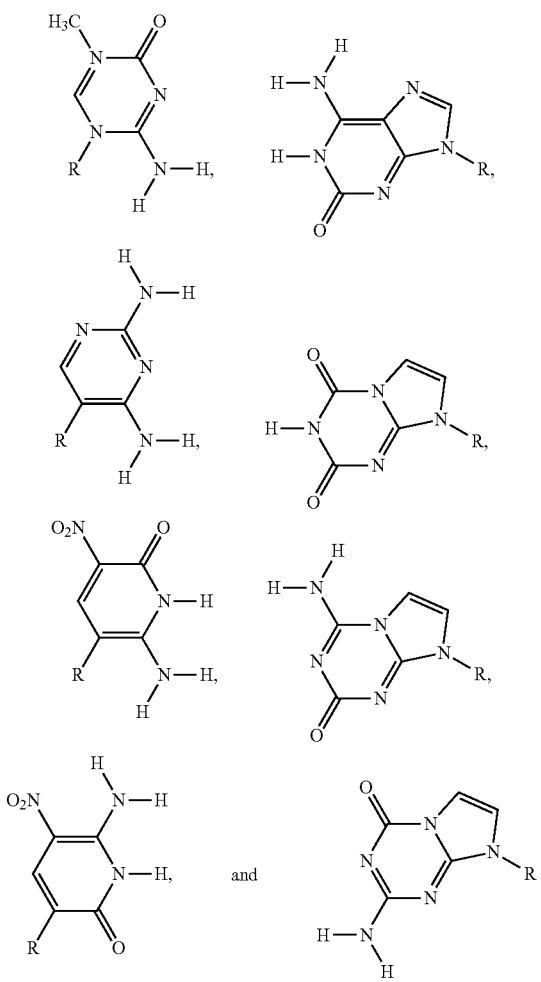

wherein R is the point of attachment of said nucleobase to the sugar of said non-standard nucleotide, and incubating the mixture with an enzyme selected from the group consisting of a DNA polymerase, an RNA polymerase, and a reverse transcriptase, and triphosphates that said enzyme incorporates opposite each of the nucleotides in said primers and said amplified oligonucleotide sequence.

2. The process of claim 1, wherein said non-standard nucleobase is selected from the group consisting of

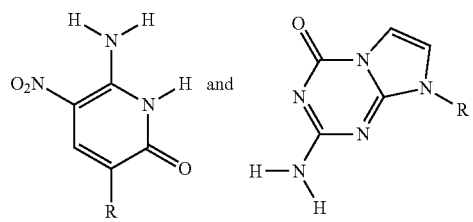

wherein R is the point of attachment of said nucleobase to the sugar of said non-standard nucleotide.

3. The process of claim 1, wherein said enzyme is selected from the group consisting of Phusion, Vent and Deep Vent.

4. The process of claim 1, wherein the pH is adjusted to optimize the melting temperature of an amplicon duplex comprising said amplified oligonucleotide sequence.

5. The process of claim 4, wherein said pH is between 6.5 and 7.5.

6. The process of claim 1, wherein multiple oligonucleotide sequences are amplified at the same time.

7. A process for amplifying an oligonucleotide sequence, said process comprising contacting said oligonucleotide sequence in aqueous solution with a forward primer comprising a first part at its 5'-end and a second part at its 3'-end, a reverse primer comprising a first part at its 5'-end and a second part at its 3'-end, a forward external primer identical in sequence to a segment within the first part of the forward primer, and a reverse external primer identical in sequence to a segment within the first part of the reverse primer, wherein the second part of said forward primer is complementary to a region at the 3'-end of said oligonucleotide sequence, wherein the second part of the reverse primer is identical in sequence to a region at the 5'-end of said oligonucleotide sequence and incubating the mixture with an enzyme selected from the group consisting of a DNA polymerase, an RNA polymerase, and a reverse transcriptase, and triphosphates that said enzyme incorporates opposite each of the nucleotides in said primers and said amplified oligonucleotide sequence, and wherein said forward external primer and reverse external primer have independently selected sequences that contain at least two non-standard nucleotides incorporating a nucleobase selected from the group consisting of

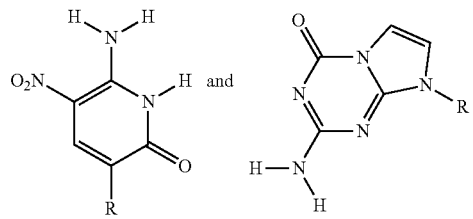

wherein R is the point of attachment of said nucleobase to the sugar of said non-standard nucleotide.

8. The process of claim 7, wherein said enzyme is selected from the group consisting of Phusion, Vent and Deep Vent.

9. The process of claim 7, wherein the pH is adjusted to optimize the melting temperature of an amplicon duplex comprising said amplified oligonucleotide.

10. The process of claim 9, wherein said pH is between 6.5 and 7.5.

11. The process of claim 7, wherein said non-standard nucleotides are adjacent in said sequence.

12. A process for amplifying an oligonucleotide sequence, said process comprising contacting said oligonucleotide sequence in aqueous solution with a forward primer comprising a first part at its 5'-end and a second part at its 3'-end, a reverse primer comprising a first part at its 5'-end and a second part at its 3'-end, a forward external primer identical in sequence to a segment within the first part of the forward primer, and a reverse external primer identical in sequence to a segment within the first part of the reverse primer, wherein the second part of said forward primer is complementary to a region at the 3'-end of said oligonucleotide sequence, wherein the second part of the reverse primer is identical in sequence to a region at the 5'-end of said oligonucleotide sequence, wherein the forward external primer and reverse external primer have independently selected sequences that contain at least one non-standard nucleotide that implements a hydrogen bonding pattern selected from the group consisting of pyADA, puDAD, pyAAD, puDDA, pyDAD, puADA, puDDA, and pyDDA, and incubating the mixture with an enzyme selected from the group consisting of a DNA polymerase, an RNA polymerase, and a reverse transcriptase, and triphosphates that said enzyme incorporates opposite each of the nucleotides in said primers and said amplified oligonucleotide sequence, wherein multiple oligonucleotide sequences are amplified at the same time.

13. The process of claim 12, wherein said enzyme is selected from the group consisting of Phusion, Vent and Deep Vent.

14. The process of claim 13, wherein the pH is adjusted to optimize the melting temperature of an amplicon duplex comprising said amplified oligonucleotide sequence.

15. The process of claim 14, wherein said pH is between 6.5 and 7.5.

16. A process for amplifying an oligonucleotide sequence, said process comprising contacting said oligonucleotide sequence in aqueous solution with a forward primer comprising a first part at its 5'-end and a second part at its 3'-end, a reverse primer comprising a first part at its 5'-end and a second part at its 3'-end, a forward external primer identical in sequence to a segment within the first part of the forward primer, and a reverse external primer identical in sequence to a segment within the first part of the reverse primer, wherein the second part of said forward primer is complementary to a region at the 3'-end of said oligonucleotide sequence, wherein the second part of the reverse primer is identical in sequence to a region at the 5'-end of said oligonucleotide sequence, wherein the forward external primer and reverse external primer have independently selected sequences that contain at least one non-standard nucleotide that implements a hydrogen bonding pattern selected from the group consisting of pyDDA, puADD, pyADA, puDAD, pyAAD, puDDA, pyADD, puDAA, pyDAD, puADA, pyDDA and puAAD, and incubating the mixture with an enzyme selected from the group consisting of a DNA polymerase, an RNA polymerase, and a reverse transcriptase, and triphosphates that said enzyme incorporates opposite each of the nucleotides in said primers and said amplified oligonucleotide sequence.

17. The process of claim 16, wherein said enzyme is selected from the group consisting of Phusion, Vent and Deep Vent.

18. The process of claim 16, wherein the pH is adjusted to optimize the melting temperature of an amplicon duplex comprising said amplified oligonucleotide sequence.

19. The process of claim 18, wherein said pH is between 6.5 and 7.5.

20. The process of claim 17, wherein multiple oligonucleotide sequences are amplified at the same time.

\* \* \* \* \*

UNITED STATES PATENT AND TRADEMARK OFFICE
CERTIFICATE OF CORRECTION

PATENT NO. : 8,614,072 B2
APPLICATION NO. : 12/999138
DATED : December 24, 2013
INVENTOR(S) : Steven A. Benner and Zunyi Yang It is certified that error appears in the above-identified patent and that said Letters Patent is hereby corrected as shown below:

In the Specification

Column 4,
Line 2, "in Example 5" should read --in Example 5.--.
Line 53, "reactions" should read --reactions.--.

Column 7,
Line 62, "shows showed" should read --show--.

Column 10,
Line 22, "PCRs generates" should read --PCRs generate--.
Line 36, "5'-CAGGAAGGAGCGATCGC-3'" should read
    --5'-CAGGAAGGAGCGATCGC-3'--.
Lines 40-41, "5'-CAGGAAGGAGCPATCPC-3'" should read
    --5'-CAGGAAGGAGCPATCPC-3'--.
Lines 41-42, "5'-CAGGAAGGAGZGATZGC-3'" should read
    --5'-CAGGAAGGAGZGATZGC-3'--.

Column 11,
Line 34, "below than that" should read --below that--.
Line 43, "with that with type B" should read --with that of type B--.

Column 13,
Lines 3-4, "may caused" should read --may be caused--.

Signed and Sealed this
Twenty-eighth Day of October, 2014

Michelle K. Lee
*Deputy Director of the United States Patent and Trademark Office*

SEQUENCE LISTING

```
<160> NUMBER OF SEQ ID NOS: 37

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
caggaaggag cgatcgcaac gcgtatcgat ggtacc                                36

<210> SEQ ID NO 2
<211> LENGTH: 36
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: p= a nonstandard nucleotide of the instant
      invention
<220> FEATURE:
<221> NAME/KEY: misc_feature
<222> LOCATION: (8)..(8)
<223> OTHER INFORMATION: p= a nonstandard nucleotide of the instant
      invention
<220> FEATURE:
<221> NAME/KEY: misc_feature
<222> LOCATION: (12)..(12)
<223> OTHER INFORMATION: p= a nonstandard nucleotide of the instant
      invention
<220> FEATURE:
<223> OTHER INFORMATION: Synthetic

<400> SEQUENCE: 2
cagnaagnag cnatcgcaac gcgtatcgat ggtacc                                36

<210> SEQ ID NO 3
<211> LENGTH: 47
<212> TYPE: DNA
<213> ORGANISM: Artificial Sequence
<220> FEATURE:
```

<223> OTHER INFORMATION: Synthetic

<400> SEQUENCE: 3
ccatgggaga ccgcggtggg cccggccggg taccatcgat acgcgtt            47

<210> SEQ ID NO 4
<211> LENGTH: 47
<212> TYPE: DNA
<213> ORGANISM: Artificial Sequence
<220> FEATURE:
<223> OTHER INFORMATION: Synthetic

<400> SEQUENCE: 4
aacgcgtatc gatggtaccc ggccgggccc accgcggtct cccatgg            47

<210> SEQ ID NO 5
<211> LENGTH: 34
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (7)..(7)
<223> OTHER INFORMATION: a nonstandard nucleotide of the instant
      invention
<220> FEATURE:
<221> NAME/KEY: misc_feature
<222> LOCATION: (12)..(12)
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<223> OTHER INFORMATION: Synthetic

<400> SEQUENCE: 5
ctangacnac gnactnccca tgggagaccg cggt            34

<210> SEQ ID NO 6
<211> LENGTH: 34
<212> TYPE: DNA
<213> ORGANISM: Artificial Sequence
<220> FEATURE:
<223> OTHER INFORMATION: Synthetic

<400> SEQUENCE: 6
ctaggacgac ggactgccca tgggagaccg cggt            34

<210> SEQ ID NO 7
<211> LENGTH: 17
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (7)..(7)
<223> OTHER INFORMATION: a nonstandard nucleotide of the instant
      invention
<220> FEATURE:
<221> NAME/KEY: misc_feature
<222> LOCATION: (12)..(12)

-continued

```
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<223> OTHER INFORMATION: Synthetic

<400> SEQUENCE: 7
ctangacnac gnactnc                                                    17

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
ctaggacgac ggactgc                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic

<400> SEQUENCE: 9
caggaaggag cgatcgc                                                    17

<210> SEQ ID NO 10
<211> LENGTH: 17
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (7)..(7)
<223> OTHER INFORMATION: a nonstandard nucleotide of the instant
      invention
<220> FEATURE:
<221> NAME/KEY: misc_feature
<222> LOCATION: (12)..(12)
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<223> OTHER INFORMATION: Synthetic

<400> SEQUENCE: 10
cagnaagnag cnagcnc                                                    17

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
```
ggtaccatcg atacgcgtt                                                    19

<210> SEQ ID NO 12
<211> LENGTH: 36
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: a nonstandard nucleotide of the instant
      invention
<220> FEATURE:
<221> NAME/KEY: misc_feature
<222> LOCATION: (6)..(6)
<223> OTHER INFORMATION: a nonstandard nucleotide of the instant
      invention
<220> FEATURE:
<221> NAME/KEY: misc_feature
<222> LOCATION: (10)..(10)
<223> OTHER INFORMATION: a nonstandard nucleotide of the instant
      invention
<220> FEATURE:
<221> NAME/KEY: misc_feature
<222> LOCATION: (11)..(11)
<223> OTHER INFORMATION: a nonstandard nucleotide of the instant
      invention
<220> FEATURE:
<221> NAME/KEY: misc_feature
<222> LOCATION: (14)..(14)
<223> OTHER INFORMATION: a nonstandard nucleotide of the instant
      invention
<220> FEATURE:
<221> NAME/KEY: misc_feature
<222> LOCATION: (15)..(15)
<223> OTHER INFORMATION: a nonstandard nucleotide of the instant
      invention
<220> FEATURE:
<221> NAME/KEY: misc_feature
<222> LOCATION: (20)..(20)
<223> OTHER INFORMATION: a nonstandard nucleotide of the instant
      invention
<220> FEATURE:
<221> NAME/KEY: misc_feature
<222> LOCATION: (22)..(22)
<223> OTHER INFORMATION: a nonstandard nucleotide of the instant
      invention
<220> FEATURE:
<223> OTHER INFORMATION: Synthetic

<400> SEQUENCE: 12
gngatngctn nttnntgaan gngtatcgat ggtacc                                 36

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcgaattaac cctcactaaa g                                                 21

<210> SEQ ID NO 14
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<221> NAME/KEY: misc_feature
<222> LOCATION: (27)..(27)
<223> OTHER INFORMATION: a nonstandard nucleotide of the instant -continued

```
      invention
<220> FEATURE:
<223> OTHER INFORMATION: Synthetic

<400> SEQUENCE: 14
gcgtaatacg actcactata gacganncta ctttagtgag ggttaattcg c          51

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
gcgaattaac cctcactaaa g                                           21

<210> SEQ ID NO 16
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<221> NAME/KEY: misc_feature
<222> LOCATION: (27)..(27)
<223> OTHER INFORMATION: a nonstandard nucleotide of the instant
      invention
<220> FEATURE:
<223> OTHER INFORMATION: Synthetic

<400> SEQUENCE: 16
gcgtaatacg actcactata gacganncta ctttagtgag ggttaattcg c          51

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
gcgtaatacg actcactata g                                           21

<210> SEQ ID NO 18
<211> LENGTH: 51
<212> TYPE: DNA
<213> ORGANISM: Artificial Sequence
<220> FEATURE:
<223> OTHER INFORMATION: Synthetic

<400> SEQUENCE: 18
gcgtaatacg actcactata gacgagcgta ctttagtgag ggttaattcg c          51

<210> SEQ ID NO 19
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<223> OTHER INFORMATION: Synthetic

<400> SEQUENCE: 19
```

```
gcgtaatacg actcactata gacgancgta ctttagtgag ggttaattcg c          51
```

<210> SEQ ID NO 20
<211> LENGTH: 51
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<221> NAME/KEY: misc_feature
<222> LOCATION: (26)..(26)
<223> OTHER INFORMATION: a nonstandard nucleotide of the instant
      invention
<220> FEATURE:
<223> OTHER INFORMATION: Synthetic

<400> SEQUENCE: 20

```
gcgtaatacg actcactata gacganncta ctttagtgag ggttaattcg c          51
```

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21

```
gcgaattaac cctcactaaa g                                           21
```

<210> SEQ ID NO 22
<211> LENGTH: 24
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: a nonstandard nucleotide of the instant
      invention
<220> FEATURE:
<221> NAME/KEY: misc_feature
<222> LOCATION: (5)..(5)
<223> OTHER INFORMATION: a nonstandard nucleotide of the instant
      invention
<220> FEATURE:
<221> NAME/KEY: misc_feature
<222> LOCATION: (10)..(10)
<223> OTHER INFORMATION: a nonstandard nucleotide of the instant
      invention
<220> FEATURE:
<221> NAME/KEY: misc_feature
<222> LOCATION: (14)..(14)
<223> OTHER INFORMATION: a nonstandard nucleotide of the instant
      invention
<220> FEATURE:
<221> NAME/KEY: misc_feature
<222> LOCATION: (18)..(18)
<223> OTHER INFORMATION: a nonstandard nucleotide of the instant
      invention
<220> FEATURE:
<221> NAME/KEY: misc_feature
<222> LOCATION: (22)..(22)
<223> OTHER INFORMATION: a nonstandard nucleotide of the instant
      invention
<220> FEATURE:
<223> OTHER INFORMATION: Synthetic

<400> SEQUENCE: 22

```
tntanatttn tatntatnta tnat                                        24
```

```
<210> SEQ ID NO 23
<211> LENGTH: 43
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: a nonstandard nucleotide of the instant
      invention
<220> FEATURE:
<221> NAME/KEY: misc_feature
<222> LOCATION: (5)..(5)
<223> OTHER INFORMATION: a nonstandard nucleotide of the instant
      invention
<220> FEATURE:
<221> NAME/KEY: misc_feature
<222> LOCATION: (10)..(10)
<223> OTHER INFORMATION: a nonstandard nucleotide of the instant
      invention
<220> FEATURE:
<221> NAME/KEY: misc_feature
<222> LOCATION: (14)..(14)
<223> OTHER INFORMATION: a nonstandard nucleotide of the instant
      invention
<220> FEATURE:
<221> NAME/KEY: misc_feature
<222> LOCATION: (18)..(18)
<223> OTHER INFORMATION: a nonstandard nucleotide of the instant
      invention
<220> FEATURE:
<221> NAME/KEY: misc_feature
<222> LOCATION: (22)..(22)
<223> OTHER INFORMATION: a nonstandard nucleotide of the instant
      invention
<220> FEATURE:
<223> OTHER INFORMATION: Synthetic

<400> SEQUENCE: 23
tntanatttn tatntatnta tnatgacagc cccggatgag aac                    43

<210> SEQ ID NO 24
<211> LENGTH: 41
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(17)
<223> OTHER INFORMATION: a nonstandard nucleotide of the instant
      invention
<220> FEATURE:
<223> OTHER INFORMATION: Synthetic

<400> SEQUENCE: 24
acnctcanta aangganaca agaattgcaa cagctcgatt g                     41

<210> SEQ ID NO 25
<211> LENGTH: 19
<212> TYPE: DNA
<213> ORGANISM: Artificial Sequence
<220> FEATURE:
<221> NAME/KEY: misc_feature
```

-continued

```
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(17)
<223> OTHER INFORMATION: a nonstandard nucleotide of the instant
      invention
<220> FEATURE:
<223> OTHER INFORMATION: Synthetic

<400> SEQUENCE: 25
acnctcanta aangganac                                                    19

<210> SEQ ID NO 26
<211> LENGTH: 24
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (9)..(9)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<221> NAME/KEY: misc_feature
<222> LOCATION: (21)..(21)
<223> OTHER INFORMATION: a nonstandard nucleotide of the instant
      invention
<220> FEATURE:
<223> OTHER INFORMATION: Synthetic

<400> SEQUENCE: 26
aaantatant aanatntata ntag                                              24

<210> SEQ ID NO 27
<211> LENGTH: 43
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: a nonstandard nucleotide of the instant
      invention
<220> FEATURE:
<221> NAME/KEY: misc_feature
<222> LOCATION: (9)..(9)
<223> OTHER INFORMATION: a nonstandard nucleotide of the instant
      invention
<220> FEATURE:
<221> NAME/KEY: misc_feature
<222> LOCATION: (13)..(13)
```

```
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<221> NAME/KEY: misc_feature
<222> LOCATION: (21)..(21)
<223> OTHER INFORMATION: a nonstandard nucleotide of the instant
      invention
<220> FEATURE:
<223> OTHER INFORMATION: Synthetic

<400> SEQUENCE: 27
aaantatant aanatntata ntagccccag ttgccgtcta gga                    43

<210> SEQ ID NO 28
<211> LENGTH: 42
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(17)
<223> OTHER INFORMATION: a nonstandard nucleotide of the instant
      invention
<220> FEATURE:
<223> OTHER INFORMATION: Synthetic

<400> SEQUENCE: 28
acnctcanta aangganacc ggacatactc tgtttggcac tt                     42

<210> SEQ ID NO 29
<211> LENGTH: 19
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(17)
<223> OTHER INFORMATION: a nonstandard nucleotide of the instant
      invention
<220> FEATURE:
<223> OTHER INFORMATION: Synthetic

<400> SEQUENCE: 29
```
acnctcanta aangganac                                               19

<210> SEQ ID NO 30
<211> LENGTH: 24
<212> TYPE: DNA
<213> ORGANISM: Artificial Sequence
<220> FEATURE:
<221> NAME/KEY: misc_feature
<222> LOCATION: (7)..(7)
<223> OTHER INFORMATION: a nonstandard nucleotide of the instant
      invention
<220> FEATURE:
<221> NAME/KEY: misc_feature
<222> LOCATION: (9)..(9)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (19)..(19)
<223> OTHER INFORMATION: a nonstandard nucleotide of the instant
      invention
<220> FEATURE:
<221> NAME/KEY: misc_feature
<222> LOCATION: (23)..(23)
<223> OTHER INFORMATION: a nonstandard nucleotide of the instant
      invention
<220> FEATURE:
<223> OTHER INFORMATION: Synthetic

<400> SEQUENCE: 30
gtatttnant aantaattna ttna                                         24

<210> SEQ ID NO 31
<211> LENGTH: 45
<212> TYPE: DNA
<213> ORGANISM: Artificial Sequence
<220> FEATURE:
<221> NAME/KEY: misc_feature
<222> LOCATION: (7)..(7)
<223> OTHER INFORMATION: a nonstandard nucleotide of the instant
      invention
<220> FEATURE:
<221> NAME/KEY: misc_feature
<222> LOCATION: (9)..(9)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (19)..(19)
<223> OTHER INFORMATION: a nonstandard nucleotide of the instant
      invention
<220> FEATURE:
<221> NAME/KEY: misc_feature
<222> LOCATION: (23)..(23)
<223> OTHER INFORMATION: a nonstandard nucleotide of the instant
      invention
<220> FEATURE:
<223> OTHER INFORMATION: Synthetic

<400> SEQUENCE: 31
gtatttnant aantaattna ttnatcctcc ttatgcctct atcat                  45

<210> SEQ ID NO 32
<211> LENGTH: 40

```
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(27)
<223> OTHER INFORMATION: a nonstandard nucleotide of the instant
      invention
<220> FEATURE:
<223> OTHER INFORMATION: Synthetic

<400> SEQUENCE: 32
acnctcanta aangganacc cgcgctttga tcaagagtcc                              40

<210> SEQ ID NO 33
<211> LENGTH: 19
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a nonstandard nucleotide of the instant
      invention
<220> FEATURE:
<221> NAME/KEY: misc_feature
<222> LOCATION: (8)..(8)
<223> OTHER INFORMATION: a nonstandard nucleotide of the instant
      invention
<220> FEATURE:
<221> NAME/KEY: misc_feature
<222> LOCATION: (13)..(13)
<223> OTHER INFORMATION: a nonstandard nucleotide of the instant
      invention
<220> FEATURE:
<221> NAME/KEY: misc_feature
<222> LOCATION: (17)..(27)
<223> OTHER INFORMATION: a nonstandard nucleotide of the instant
      invention
<220> FEATURE:
<223> OTHER INFORMATION: Synthetic

<400> SEQUENCE: 33
acnctcanta aangganac                                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
acgctcagta aagggagac                                                    19
```

```
<210> SEQ ID NO 35
<211> LENGTH: 17
<212> TYPE: DNA
<213> ORGANISM: Artificial Sequence
<220> FEATURE:
<223> OTHER INFORMATION: Synthetic

<400> SEQUENCE: 35
caggaaggag cgatcgc                                                    17

<210> SEQ ID NO 36
<211> LENGTH: 17
<212> TYPE: DNA
<213> ORGANISM: Artificial Sequence
<220> FEATURE:
<221> NAME/KEY: misc_feature
<222> LOCATION: (12)..(12)
<223> OTHER INFORMATION: a nonstandard nucleotide of the instant
      invention
<220> FEATURE:
<221> NAME/KEY: misc_feature
<222> LOCATION: (16)..(16)
<223> OTHER INFORMATION: a nonstandard nucleotide of the instant
      invention
<220> FEATURE:
<223> OTHER INFORMATION: Synthetic

<400> SEQUENCE: 36
caggaaggag cnatcnc                                                    17

<210> SEQ ID NO 37
<211> LENGTH: 17
<212> TYPE: DNA
<213> ORGANISM: Artificial Sequence
<220> FEATURE:
<221> NAME/KEY: misc_feature
<222> LOCATION: (11)..(11)
<223> OTHER INFORMATION: a nonstandard nucleotide of the instant
      invention
<220> FEATURE:
<221> NAME/KEY: misc_feature
<222> LOCATION: (15)..(15)
<223> OTHER INFORMATION: a nonstandard nucleotide of the instant
      invention
<220> FEATURE:
<223> OTHER INFORMATION: Synthetic

<400> SEQUENCE: 37
caggaaggag ngatngc                                                    17
```